United States Patent
Markus et al.

(10) Patent No.: US 9,079,152 B2
(45) Date of Patent: Jul. 14, 2015

(54) ENCAPSULATED ESSENTIAL OILS

(75) Inventors: Arie Markus, Shoham (IL); Charles Linder, Rehovot (IL)

(73) Assignee: BEN GURION UNIVERSITY OF THE NEGEV RESEARCH AND DEVELOPMENT AUTHORITY (IL)

( * ) Notice: Subject to any disclaimer, the term of this patent is extended or adjusted under 35 U.S.C. 154(b) by 1241 days.

(21) Appl. No.: 10/556,633

(22) PCT Filed: May 6, 2004

(86) PCT No.: PCT/IL2004/000384
§ 371 (c)(1),
(2), (4) Date: Nov. 10, 2005

(87) PCT Pub. No.: WO2004/098767
PCT Pub. Date: Nov. 18, 2004

(65) Prior Publication Data
US 2007/0042182 A1     Feb. 22, 2007

(51) Int. Cl.
B32B 9/00         (2006.01)
A01N 25/00        (2006.01)
B01J 13/16        (2006.01)
A01N 65/00        (2009.01)

(52) U.S. Cl.
CPC .................. *B01J 13/16* (2013.01); *A01N 65/00* (2013.01); *Y10T 428/2984* (2015.01)

(58) Field of Classification Search
USPC ............. 428/402–402.24; 427/213.3–213.36, 427/331, 389.9, 212, 213–213.36, 483, 427/256; 264/4–4.7, 534, 5, 41; 424/400, 424/408, 450, 451, 455, 93.7, 184.1, 497, 424/489, 501, 490, 491, 4, 92, 493, 494, 424/495
See application file for complete search history.

(56) References Cited

U.S. PATENT DOCUMENTS

| | | | |
|---|---|---|---|
| 3,577,515 A | 5/1971 | Vandegaer | |
| 3,754,062 A * | 8/1973 | Kobayashi | 264/4 |
| 3,957,964 A | 5/1976 | Grimm, III | |
| 4,021,595 A * | 5/1977 | Kiritani et al. | 503/213 |
| 4,046,741 A | 9/1977 | Scher | |
| 4,071,614 A | 1/1978 | Grimm, III | |
| 4,140,516 A | 2/1979 | Scher | |
| 4,285,720 A | 8/1981 | Scher | |
| 4,417,916 A | 11/1983 | Beestman et al. | |
| 4,563,212 A * | 1/1986 | Becher et al. | 71/11 |
| 4,707,355 A * | 11/1987 | Wilson | 424/84 |
| 4,851,227 A | 7/1989 | Markus et al. | |
| 5,114,824 A * | 5/1992 | Tan et al. | 430/137.12 |
| 5,232,769 A | 8/1993 | Yamato et al. | |
| 5,411,992 A | 5/1995 | Eini et al. | |
| 5,686,113 A * | 11/1997 | Speaker et al. | 424/490 |
| 5,753,264 A | 5/1998 | Magdassi et al. | |
| 5,925,464 A | 7/1999 | Mulqueen et al. | |
| 6,200,572 B1 | 3/2001 | Vernin | |
| 6,238,677 B1 | 5/2001 | Fanta et al. | |
| 6,414,036 B1 | 7/2002 | Ninkov | |
| 6,653,042 B1 * | 11/2003 | Fukino et al. | 430/270.1 |
| 2002/0160035 A1 | 10/2002 | Fotinos | |
| 2003/0222378 A1 * | 12/2003 | Xing et al. | 264/432 |

FOREIGN PATENT DOCUMENTS

| | | |
|---|---|---|
| CA | 1044134 | 12/1978 |
| CA | 1179682 A | 12/1984 |
| CN | 1430981 | 7/2003 |
| EP | 0611253 A1 | 8/1994 |
| GB | 1371179 | 10/1974 |
| GB | 1513614 | 6/1978 |
| JP | 2-40233 A | 2/1990 |
| WO | 97/14308 | 4/1997 |
| WO | 98/51320 | 11/1998 |
| WO | 03/101606 | 12/2003 |

OTHER PUBLICATIONS

Markus, A. *Advances in the technology of controlled release pesticide formulations in Microencapsulation methods and industrial application.* p. 73-93. Marcel Dekker Inc. 1996.

* cited by examiner

*Primary Examiner* — James J Seidleck
*Assistant Examiner* — S. Camilla Pourbohloul
(74) *Attorney, Agent, or Firm* — Whitmyer IP Group LLC

(57) ABSTRACT

The invention provides a process for the preparation of essential oil microcapsules comprising dissolving a di- or polyisocyanate into an essential oil, emulsifying the resulting mixture in an aqueous solution containing a di- or polyamine, and or a di or polyhydroxy compound to effect encapsulation of said essential oil through interfacial polymerization, whereby there is formed a polyurea and/or polyurethane film around the essential oil droplets which film enhances the stability of said essential oil, reduces its evaporation rate and controls its release rate when applied to a substrate.

18 Claims, No Drawings

ENCAPSULATED ESSENTIAL OILS

The present application relates to microcapsules of essential oils, processes for the preparation thereof and their application as green disinfectant products for the consumer market as hard-surface cleaners, laundry detergents and softeners and as pesticides such as nontoxic larvicidal agents against mosquitoes, and as insect repellants as for example against mosquitoes, ants and other insects, and as anti viral and anti fungal agents. The invention also provides disinfectants or pesticides or repellants and larvicidal agent compositions comprising essential oils encapsulated in microcapsules, the microcapsules having an encapsulating wall formed essentially from the reaction product of di- or polyisocyanate and a polyfunctional amine optionally in the presence of a di- or polyfunctional alcohol. The invention also provides a process for encapsulating the essential oils in a microcapsular formulation comprising an aqueous phase containing a emulsifiers and suspending agents, providing an organic phase which is the essential oil containing a di or polyiisocyanate, combining the aqueous and organic phase to form an oil in water emulsion, and adding an aqueous solution of a di or polyfunctional amine and di and polyfunctional alcohols with agitation to the emulsion, whereby the amine and alcohols reacts with the isocyanate to form microcapsular envelopes about the essential oil.

More particularly, according to the present invention there is now provided a process for the preparation of essential oil microcapsules comprising dissolving a di- or polyisocyanate into an essential oil, emulsifying the resulting mixture in an aqueous solution containing a di- or polyamine, and or a di or polyhydroxy compound to effect encapsulation of said essential oil through interfacial polymerization, whereby there is formed a polyurea and/or polyurethane film around the essential oil droplets which film enhances the stability of said essential oil, reduces its evaporation rate and controls its release rate when applied to a substrate.

In preferred embodiments of the present invention said polymerization is carried out at a temperature of between 0° C.-30° C.

Preferably said mixture further comprises a catalyst.

In preferred embodiments said aqueous solution further comprises a di- or polyalcohol and further optionally comprises a di or polyamine.

Preferably, said aqueous solution further comprises at least one emulsifier.

Also preferred is a process wherein said essential oil is encapsulated together with a further component selected from an adjuvant and an agent which enhances the properties of the essential oil and preferably said further component is sesame seed oil.

In preferred embodiments of the present invention said encapsulation is carried out at ambient conditions by dissolving a polyisocyanate into said essential oil, emulsifying the resulting mixture in an aqueous solution containing a polyamine and/or a di- or polyalcohol, wherein a preliminary reaction occurs which forms a membrane and consumes any of the polyamine present, and the slower reacting polyalcohol then reacts and forms an exterior crosslinked coating, and any remaining isocyanate is further consumed by water to form amine which reacts with any remaining isocyanate.

Alternatively, said process is carried out in an environment wherein di or polyamines are absent from the aqueous solution.

In the process of the present invention, said di- or polyisocyanate is preferably chosen from the group consisting of dicyciohexylmethane 4,4'-diisocyanate; hexamethylene 1,6-diisocyanate; isophorone diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato)cyclohexane; biuret of hexamethylene diisodyanate; urea of hexamethylene diisocyanate; trimethylenediisocyanate; propylene-1,2-diisocyanate; and butylene-1,2-diisocyanate mixtures of aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate, aromatic polyisocyanates include 2,4- and 2,6-toluene diisocyanate, naphthalene diisocyanate, diphenylmethane diisocyanate and triphenylmethane-p,p',p"-trityl triisocyanate. Suitable aromatic isocyanates are toluene diisocyanate, polymethylene polyphenylisocyanate, 2,4,4'-diphenyl ether triisocyanate, 3,3'-dimethyl-4,4'-diphenyl diisocyanate, 3,3'-dimethoxy-4,4'diphenyl diisocyanate, 1,5-naphthalene diisocyanate and 4,4',4"-triphenylmethane triisocyanate, and isophorone diisocyanate.

Preferably, said diamine or polyamine is selected from the group consisting of ethylenediamine, diethylenetriamine, propylenediamine Tetraethylenepentaamine, pentamethylene hexamine, alpha, omega-diamines, propylene-1,3-diamine, tetramethylenediamine, pentamethylenediamine and 1,6-hexamethylenediamine polyethyleneamines, diethylenetriamine, triethylenetriamine, pentaethylenehexamine, 1,3-phenylenediamine, 2,4-toluylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetraaminoanthraquinone Preferably, said di- or polyalcohol is selected from the group consisting of polyhydric alcohols, such as ethylene glycol, dietheylene glycol, propylene glycol, 1,4-butane diol, 1,4 hexane diol, dipropylene glycol, cyclohexyl 1,4 dimethanol, 1,8 octane diol and polyols such as poly(ethylene glycols), poly(propylene glycols), poly(tetramethylene glycols) with average molecular weights in the range of 200-2000, trimethylolpropane, glycerol, hexane, triols and pentaerythrytol, 1,3-phenylenedihydroxy, 2,4-toluylenedihydroxy, 4,4'-dihydroxydiphenylmethane, 1,5-dihydroxyoaphthalene, 1,3,5-trihydroxybenzene, 2,4,6-trihydroxytoluene, 1,3,6-trihydroxynaphthalene, 2,4,4'-trihydroxydiphenyl ether and hydrolyzed polyvinyl alcohols.

Preferably, said catalyst is selected from the group consisting of amino or organometallic compounds such as N,N-dimethylaminoethanol, N—N-dimethylcyclohexylamine, bis-(2-dimethylaminoethyl)ether, N,N dimethylcetylamine, diaminobicyclooctane, stannous octoate and dibutyltin dilaurate having concentration 0.1-0.3 wt. % based on diol and metal salts, tertiary amines such as triethylamine or diethylmethyl amine and metal salts of Cu, Pb, Zn, Co, Ni, Mn.

In one especially preferred embodiments of the present invention, emulsifiers, dispersants and steric barrier polymers which prevent microcapsule aggregation are used by adding them to the aqueous solution used to prepare the said microcapsules. These emulsifiers, steric barrier may be selected from the group consisting of sodium, potassium, magnesium, calcium or ammonium salts of lignin sulfonate; low and high density polyvinylalcohol, or Tween 20, 40 or 80 and suspending agents selected from the group consisting of carboxymethyl cellulose, sodium salt, Xantan gum, Karya gum and Locust bean gum polyvinylpyrrolidone (PVP), water soluble polyvinyl alcohol (PVA) with different degrees of acetate hydrolysis, with 80% to 90% hydrolysis as one of the most preferred range, another range being above 95% hydrolysis, and poly(ethoxy)nonylphenol are used to form dispersions. PVP is available at various molecular weights in the range of from about 20,000 to about 90,000. Poly(ethoxy)nonylphenols with various molecular weights depending on the length of the ethoxy chain. Poly(ethoxy)nonylphenols, polyether block copolymers, polyoxyethylene adducts of fatty alcohols, surfactants, and esters of fatty acids, such as stearates, oleates, sorbitan monostearate, sorbitan monooleate, sorbitan sesquioleate. Each of the aforementioned emulsifiers, dispersants and steric barrier polymers may be used alone or in combination. They are generally added to the aqueous solution prior to the dispersion of the non-aqueous essential oil/isocyanate or they be added during or after the interfacial polymerization in some cases.

In especially preferred embodiments of the present invention, the resulting microcapsules comprise 60 to 95% essential oils and the remainder of said microcapsules are comprised of the encapsulating walls and additives.

Preferably, the resulting microcapsules have an average size of between 10 to 100 microns.

In especially preferred embodiments of the present invention, the resulting microcapsules contain essential oils which serve as larvicides which are 0.5 to 100 microns in size and which are optionally adapted to float on water surfaces, which are not degraded by UV radiation, and which slowly release an effective dose of the essential oil pesticide encapsulated therein.

In other preferred embodiments of the present invention, the resulting microcapsules contain essential oils, which serve as larvicides which are 0.5 to 100 microns in size and which are optionally adapted to float on water surfaces, and optionally not degraded by UV radiation, and which slowly release an effective dose of the essential oil larvicide encapsulated therein.

In still further preferred embodiments of the present invention, the resulting microcapsules contain essential oils, which serve as larvicides, which are 0.5 to 100 microns in size which slowly release an effective dose of the essential oil insect repellent encapsulated therein.

Further provided according to the present invention is a process wherein the resulting microcapsules contain essential oils, which serve as larvicides which are 0.5 to 100 microns in size, which are optionally not degraded by UV radiation, and which slowly release an effective dose of the essential mosquito repellent encapsulated therein.

In another aspect of the present invention the resulting microcapsules contain essential oils which serve as replacements for chlorine-containing disinfectants in consumer products and which microcapsules possess sustained anti-microbial activity when used in hard surface cleaners, laundry detergents and softeners.

In a further aspect of the present invention, said microcapsules, after formation, are reacted with reactive amine or hydroxyl containing reagents which also contain anionic or cationic or amphoteric or hydrophilic groups which render the surface of the encapsulated essential oil microcapsules anionic, cationic or amphoteric or hydrophilic but non-charged.

In yet another aspect of the present invention, said microcapsules, after formation, are post modified by absorbing onto their surfaces monomers or polymers, which increase their hydrophilicity, or hydrophobicity, or render their surfaces anionic, cationic or amphoteric or hydrophilic but non-charged.

The present invention also provides essential oil microcapsules whenever prepared by any of the aforesaid processes.

In one embodiment of the invention microcapsules are formed by room temperature encapsulation of essential oils in polyurea and or polyurethane microcapsules by interfacial polymerization. These capsules have the characteristics to allow them to prevent evaporation or oxidation of the encapsulated essential oil and to be absorbed and maintained on the surfaces to which they are applied and have sustained release properties. The method of encapsulation and the material for the capsule membranes gives a formulation for essential oils that is of low or no toxicity and is ecologically safe [termed "green"] which overcomes the current limitations of toxicity of low efficacy of the state-of-the-art materials and technologies.

In another embodiment of the invention sustained-release microencapsulated formulations of essential oils for mosquito control are claimed as a competitive "green" alternative to currently used synthetic chemicals. The invented formulations will also yield improved performance at lower cost than other natural larvicidal agents. The micro-encapsulation by interfacial polymerization to form interfacially polyurea and polyurethane films decreases the effective concentration needed per application and to increase duration of activity. For the claimed application of larvicides the microcapsules of essential oil are micron-sized encapsulated particles of essential oils that can float on water surfaces, that are not degraded by UV radiation, and that can slowly release an effective dose.

In still another embodiment the invented microcapsules of essential oils will be applied for replacing chlorine-containing disinfectants in consumer products were good sustained anti-microbial activity is needed such as in hard surfaces cleaners and detergents in general.

In still another preferred embodiment: The encapsulation is carried out by dissolving into the essential oil a polyisocyanates based on bisphenol A, emulsifying this mixture in water containing a polyamine and di or poly alcohol (ex. polyethylene glycol [PEG]. A preliminary reaction occurs which forms a membrane and consumes all of the polyamine. The slower reacting polyalcohol is then reacted and forms and exterior cross-linked coating. Any remaining isocyanate is further consumed by water to form amine which reacts with remaining isocyanate. The final product contains only the microcapsules dispersed in water with no toxic chemical left. The solution is not purified further and other materials are added constitute the final formulation.

In still another preferred embodiment: The encapsulation is carried out by dissolving into the essential oil a polyisocyanates based on bisphenol A, emulsifying this mixture in water containing a di or poly alcohol (ex. polyethylene glycol [PEG]. A preliminary reaction occurs which forms a membrane and results in primarily a polyurethane encapsulating coating with minimal urea groups which may form by hydrolysis of the isocyanate with the water and the resulting amines reacting with remaining isocyanate groups. The final product contains only the microcapsules dispersed in water with no toxic chemical left. The solution does not need to be further purified and other materials are added constitute the final formulation.

In other preferred embodiments of the present invention said microcapsules after formation are reacted with reactive amine or hydroxyl containing reagents which also contain anionic or cationic or amphoteric or hydrophilic groups which render the surface of the encapsulated essential oil microcapsules anionic, cationic or amphoteric or hydrophilic but non-charged.

In further preferred embodiments of the present invention said microcapsules after formation are post modified by absorbing onto their surfaces monomers or polymers which increase their hydrophilicity, or hydrophobicity, or render their surfaces anionic, cationic or amphoteric or hydrophilic but non-charged.

In another embodiment the essential oil is encapsulated with adjuvants or agents which enhance the properties of the essential oils as for example sesame seed oil which contains components to enhance the properties of other essential oils to perform as larvicides or antimicrobials.

In especially preferred embodiments of the present invention the process is characterized by the room temperature encapsulation of essential oils in strong polyurea and or polyurethane microcapsules formed by interfacial polymerization. By controlling the nature and concentrations of the reactants and the conditions in which the their reactions occurs such as pH, ionic strength, temperature, emulsifiers, suspending agents the presence of solvents the size of the microcapsules and the permeability of the encapsulating barrier to the essential oil is controlled more efficiently than the other methods used to date to encapsulated the aforementioned essential oils. By this process essential oils may be made into effective green alternatives to currently used toxic chemicals and have considerably improved efficacy over non-encapsulated essential oils and essential oils encapsulated by other methods. Encapsulation is needed as non-encapsulated as products based on essential oils may be extremely sensitivity to oxidation and volatile, properties that impair their efficacy and encapsulation is needed to prevent oxidation and evaporation. Encapsulated essential oil that are cited in the state of art do not have the absorption and staying power relative to the surfaces to which they are applied and/or do not have the required sustained releasing characteristic required for a cost effective product. The releasing properties of state of art microcapsules of essential oils either are too fast or two slow or/and are not released at a constant rate. Our invented capsules have the necessary characteristics to allow them to be absorbed and maintained on the surfaces to which they are applied and have the required sustained release properties. The method of encapsulation and the material for the capsule membranes results give an ideal formulation for essential oils that overcomes the current limitations of the state-of-the-art materials and technologies as a sustained-release product, which would increase the stability and duration of activity of the active materials and lower the quantity needed and hence the production costs. This novelty of unique microcapsules of the essential oil, which confer the required absorptive and sustained release characteristics, allows to make a much sought but not achieved cost effective "green" materials as compared to synthetic chemicals.

BACKGROUND

Before the development of the modern chemical and pharmaceutical industries, essential oils were used in many areas of daily life as antiseptic and disinfectant materials in pharmaceutical and cosmetic applications, such as anti microbial (antiviral, antibacterial and antifungal) and larvicidal agents. Essential-oil-based formulations with a broad spectrum of antimicrobial activity have been shown to be relatively non-toxic to mammals, particularly to surface cleaning compositions based on essential oils that were particularly effective disinfectants and antimicrobials have been replaced with more potent synthetic chemicals and antibiotics, are cheaper and highly effective and can be used in lower concentrations. With time, however, the toxic and environmental effects of such synthetic chemicals have been revealed, and there is now an effort to replace them with the same essential oil agents that they replaced.

In the area of disinfectants for consumer products a safe alternative for synthetic chemicals and antibiotics used as disinfectants and antimicrobial agents are needed to replace chemicals now used which have been shown to be toxic to man and to the environment. Some of these disinfectants have been shown due to have chronic toxic effects, especially in children. There is a need to replace chemicals containing active chlorine and other synthetic chemicals with nontoxic natural "green" materials. Fragrant natural essential oils with little or no toxicity have shown good anti-microbial properties and, as such, are contenders for replacing chlorine-containing disinfectants. We have demonstrated for eucalyptus oil good anti-microbial activity in a laundry softening application. The failure, however of essential oil products, including current encapsulated formulations, to break into the consumer market is due to raw material prices, insufficient sustained activity, and the need for repeated application.

In the area of pesticides the present microcapsules can be used in such applications as larvicides, repellents and insecticides. With respect to larvicide applications the essential oil microcapsules for mosquito control will compete with state of art larvicidal agents [organophosphates, organochlorines, carbamates, petroleum oils, insect growth regulators (IGR) (e.g., methoprene or pyriproxyfen.

Two important reasons to control mosquitoes are to avoid nuisance biting, and to preclude the spread of mosquito-borne diseases including illnesses such as malaria, encephalitis, dengue and yellow fevers, as well as West Nile Virus. The World Health Organization estimates that more than 500 million clinical cases each year are attributable to disease agents carried and transmitted by mosquitoes. In the United States there is a recent upsurge in mosquito borne diseases which has significantly increased the commercial value of larvicides. Currently, chemical insecticides are used to control mosquitoes either as larvicide or as adulticide, even though insecticides may be detrimental to human health and are known to have harmful effects on the environment and wildlife. Biological mosquito larvicides are mainly microorganism-based products that are registered as pesticides for control of mosquito larvae outdoors. In addition to being costly, biologicails are difficult to apply efficiently because the duration of effectiveness depends primarily on the formulation of the product, environmental conditions, water quality, and mosquito species.kly 2% sprays of mineral oils.

Applications Claimed for the Use of the Invented Microcapsules:

Nontoxic larvicides, Cleaners for hard surfaces, Laundry detergents, diapers, feminine tampons Laundry softeners. Insect repellents especially to mosquitoes, and ants.

The following applications are claimed for the invented microcapsules of essential oils. The use of the microcapsules of the present invention in the given application increase the efficacy of the essential oil by lowering the quantity needed for prolonged activity thus lowering the cost of application and making the essential oil competitive with current synthetic chemicals.

1) Disinfectant and sanitizing compositions for hard surfaces such as counter tops, tiles, porcelain products (sinks and toilets), floors, windows, cutlery, glassware, dishes and dental and surgical instruments;
2) Fragrance and skin-benefit liquids for application to textile structures to improve physiological conditions of the skin;

Antimicrobial wipes that provide improved immediate germ reduction covered in the following US patents described in the section Comparison with Current State of Art for essential oils;
3) Leave-on antimicrobialcompositions that provide improved residual benefit covered in the following US patents described in the section Comparison with Current State of Art for essential oils, versus gram positive bacteria;
4) Antimicrobial compositions formulated with essential oils covered in the following US patents described in the section Comparison with Current State of Art for essential oils;
6) Disinfectant and sanitizing compositions based on essential oils covered in the following US patents described in the section Comparison with Current State of Art for esseritial oils;
7) Blooming agents in germicidal hard surface cleaning compositions;
8) Liquid detergent compositions;
9) Antimicrobial compositions with antiseptic, antiviral and larvicidal activity as treatments for cold sores, head lice, vaginal thrush, verruca, warts, and athlete's foot and as antimicrobial mouth washes and surface cleaners;
10) Lice treatment;
11) Natural pesticides;
12) Flavoring agents;
13) Fragrances;
14) Treatment of infections in man and animals;
15) Lice repellant composition;
16) Analgesic and antiphlogistic compositions;
17) Fragrance or insect-repellant agent;
18) Active agents in pharmaceuticals and cosmetics;
19) Benefit agent in extruded soap and/or detergent bars;
20) Food or tobacco additive;
21) Active agents in Pharmaceuticals and Cosmetics;
22) Hair care products; and
23) Dentifrice containing encapsulated flavoring.
24) Mosquito, ants and insect repellents
25) Mosquito larvicides
26) Anti viral agents
27) Anti fungal agents
28) Gels against gum diseases
29) Tampons for women use safe from toxic syndromes
30) Diapers Comparison with Current State of Art A review of the state of art shows that essential oils have been incorporated into many different formulations for the above-described applications. Although the encapsulation techniques have been used for such oils to improve stability, facilitate sustained release, and reduce application costs (for the same applications that we propose to develop), these efforts have, to the best of our knowledge, not resulted in commercial products that can effectively compete with currently available synthetic chemicals. The reason is that currently used essential oils, including those that have been encapsulated, do not meet one or more of the requirements described above for producing a cost-effective microencapsulated product. The drawbacks of currently available products include:
1) They do not have sufficiently long life times on the surfaces to which they are applied and/or do not give sustained released on those substrates at a continuous effective dose because of ineffective encapsulating barriers;
2) They are produced by a process that destroys or modifies many of the oil's properties; and
3) In many cases, they must be applied at a higher than cost-effective dosage to be effective and thus cost significantly more than currently available synthetic chemicals.

The patent literature on encapsulated essential oils can be divided into the following categories:
1) Patents describing all methods of encapsulation and a wide range of polymer encapsulants but giving limited examples and claims;
2) Patents based on a solid core containing the essential oils adsorbed inside, with and without subsequent coatings;
3) Encapsulation of essential oil droplets or emulsions in a polymer shell by coacervation or adsorption of preformed polymers;
4) Encapsulation of essential oil droplets or emulsions in a polymer shell by coacervation or adsorption of preformed polymers; and
5) Encapsulation in microorganisms. The closes state of art in the present patent is the encapsulation of essential oils as an a liquid core. In patents U.S. Pat. No. 3,957,964, U.S. Pat. No. 5,411,992, U.S. Pat. No. 6,414,036 describing all methods of encapsulation and a wide range of polymer encapsulants but giving limited examples and claims. None of the examples or claims relate specifically to interfacial polymerization to form polyurethanes or polyurea encapsulated essential oils.

In U.S. Pat No. 6,238,677, U.S. Pat. No. 5,753,264, U.S. Pat. No. 6,200,572, PCT/PUBLICATION-1997-07-09, A1 on the encapsulation of essential oil droplets or emulsions in a polymer shell by coacervation or adsorption of preformed polymers. These patents are not relevant to our proposed patents and practically would not have the necessary sustained release or required stability in our applications because of the nature of the microcapsule Walls.

In U.S. Pat. No. 5,232,769 pertains to the encapsulation of essential oil droplets or emulsions in a polymer shell by interfacial polymerization of monomers such as melamine or urea dissolved in essential oil droplets and cross-linked interfacially by formalin. There is no sustained release in this case, and the microcapsules in the formalin, melamine or urea example are hard and would give an unpleasant sensation to a surface to which it was applied.

Interfacial polymerization to form polyurea and polyurethane microcapsules have been widely applied to the encapsulation of pesticides and herbicides [see A. Markus, Advances in the technology of controlled release pesticide formulations" in Micro-encapsulation: Methods and Industrial Applications, S. Benita (Ed), 1996, pp. 73-91 and U.S. Pat. No. 4,851,227 Jul. 25, 1989]. These methods and materials have not been used however in the encapsulation of the essential oils and it is indeed surprising that they work well for non-toxic essential oils. Use of interfacial condensation to encapsulate substances such as pharmaceuticals, pesticides and herbicides is discussed in U.S. Pat. No. 3,577,515, issued on May 4, 1971. The encapsulation process involves two immiscible liquid phases, one being dispersed in the other by agitation, and the subsequent polymerization of monomers from each phase at the interface between the bulk (continuous) phase, and the dispersed droplets. The immiscible liquids are typically water and an organic solvent. Polyurethanes and polyureas are included in the types of materials suitable for producing the microcapsules. The use of emulsifying agents (also known as suspending or dispersing agents) is also discussed. The United States patent discloses formation of microcapsules comprising a polymeric sphere and a liquid centre, ranging from 30 micron to 2 mm in diameter, depending on monomers and solvents used.

Use of interfacial condensation to encapsulate substances such as pharmaceuticals, pesticides and herbicides is discussed in U.S. Pat. No. 3,577,515, issued on May 4, 1971. The encapsulation process involves two immiscible liquid phases, one being dispersed in the other by agitation, and the subsequent polymerization of monomers from each phase at the interface between the bulk (continuous) phase, and the dispersed droplets. The immiscible liquids are typically water and an organic solvent. Polyurethanes and polyureas are included in the types of materials suitable for producing the microcapsules. The use of emulsifying agents (also known as suspending or dispersing agents) is also discussed. The United States patent discloses formation of microcapsules comprising a polymeric sphere and a liquid centre, ranging from 30 micron to 2 mm in diameter, depending on monomers and, solvents used.

United Kingdom Patent No. 1,371,179 discloses the preparation of polyurea capsules for containing dyes, inks, chemical reagents, pharmaceuticals, flavouring materials, fungicides, bactericides and pesticides such as herbicides and insecticides. The capsules are prepared from various di- and polyisocyanates in a dispersed organic phase. Some of the isocyanate present reacts to yield an amine which reacts further with remaining isocyanate at the interface with water and subsequently polymerizes to form a polyurea shell. The aqueous phase also contains a surfactant, for example an ethoxylated nonylphenol or a polyethylene glycol ether of a linear alcohol. In addition, the aqueous phase contains protective colloids, typically polyacrylates, methylcellulose and PVA. Particle sizes as low as 1 micron are exemplified. Encapsulation of insect hormones and mimics are among the systems mentioned.

U.S. Pat. No. 4,046,741 and U.S. Pat. No. 4,140,516 appear to relate to developments of the process disclosed in United Kingdom Patent No. 1,371,179. According to U.S. Pat. No. 4,046,741, a problem with microcapsules is instability caused by evolution of carbon dioxide from residual isocyanate entrapped the microcapsules. U.S. Pat. No. 4,046,741 discloses a post-treatment of polyurea microcapsules with ammonia or an amine such as diethylamine. This removes the residual isocyanate, allowing subsequent storage of the microcapsules at lower pH's without generation of carbon dioxide. U.S. Pat. No. 4,140,516 discloses the use of quaternary salts as phase transfer catalysts to speed up the formation of polyurea microcapsules.

Canadian Patent No. 1,044,134 is concerned with micro-encapsulation of insecticides, particularly pyrethroids. The insecticide is dissolved, together with a polyisocyanate, in a water-immiscible organic solvent. The solution in organic solvent is then dispersed in water by agitation, and a polyfunctional amine is added while agitation is continued. The polyisocyanate and the polyfunctional amine react to form a polyurea shell wall that surrounds the dispersed droplets containing the insecticide.

Micro-encapsulation (or encapsulation) of active agents is a well-known method to control their release and improve shelf life and duration of activity. Sustained release formulations based on encapsulation of the active agent can produce a more cost effective product than the non-encapsulated product. Many other hydrophobic or non-water soluble agents such as pesticide have been successfully encapsulated by a variety of methods. Microcapsules are flowable powders or powders having particle diameters in the range of approximately 0.1 microns to 1,000 microns. They are prepared using a range of coating processes in which finely distributed solid, liquid and even gaseous substances are used. Polymers are conventionally used as the coating or wall material. Basically, microcapsules therefore consist of two disparate zones, the core zone and the coating zone. Preparation processes that are suitable for micro-encapsulation include: phase separation processes (simple and complex coacervation), interface polymerization processes (polycondehsation or polyaddition from dispersions) and physicomechanical processes (fluidized-bed process, spray drying). An essential disadvantage of conventional micro-encapsulation is the fact that the preparation is relatively complicated.

The encapsulation of materials such as medications, pesticides (including insecticides, nematocides, herbicides, fungicides and microbiocides), preservatives, vitamins, and flavoring agents is desirable for a number of reasons. In the case of medicatioris and pesticides, encapsulation may provide controlled release of the active material. In the case of vitamins, the encapsulation may be carried out to protect the vitamin from oxidation and thus to extend its shelf life. In the case of a flavoring agent, encapsulation may be carried out to place the flavoring agent in an easily metered form, which will release the flavoring agent in response to a controllable stimulus, such as the addition of water. It is generally known to skilled practitioners in the field of flavor encapsulation that current practical commercial processes for producing stable, dry flavors are generally limited to spray drying and extrusion fixation. The former process requires the emulsification or solubilization of the flavor in a liquid carrier containing the encapsulating solids, followed by drying in a high-temperature, high-velocity gas stream and collection as a low-bulk-density solid.

While spray drying accounts for the majority of commercial encapsulated materials, several limitations of the process are evident. Low-molecular-weight components of complex or natural flavor mixtures may be lost or disproportionate during the process. The resultant flavor-carriers are porous and difficult to handle. In addition, deleterious chemical reactions such as oxidation can result on surfaces exposed during and after drying. The final product, a dry free-flowing powder, will release the encapsulant rapidly upon rehydration whether rapid release is desired or not.

There are encapsulated forms of larvicides based on materials other than essential oils. For example ALTOSID® by Wellmark International is a micro-encapsulated mosquito larvicide has been used in the United States to reduce mosquito infestations by preventing immature mosquito larvae from becoming disease-spreading adults. The active ingredient, methoprene, is an insect growth regulator that interferes with normal mosquito development.

Microcapsule Characteristics of the Invention

Encapsulation is needed for sustained release and improved stability of essential oils, both characteristics that are required to make a product cost effective. Products based, on essential oils may be extremely sensitivity to oxidation and volatile, properties that impair their efficacy and encapsulation is needed to prevent oxidation and evaporation. Many "green" materials, including essential oils, are less efficient and more expensive than the synthetic chemicals they seek to replace. There is thus a need to produce these "green" materials with a smaller effective dosage and increased effectiveness by enhancing the duration of activity per dose. The products that we are proposing are sustained release formulations will meet these needs in the form of encapsulated essential oils. When applied to a given substrate the oils will be released at a constant rate over a long period of time, thus increasing the duration of activity per dose and lowering the quantity needed and hence reducing the cost of the product. The encapsulation also will stabilize the essential oils with respect to oxidation and evaporation, a step that is required for product formulation, shelf life, application and duration of activity upon application.

The invented microcapsules are micron-sized microcapsules containing a liquid core of essential oil by a cost-effective process that has a high encapsulation efficiency with low oil loss. The resultant microcapsules release an effective dose at a constant unchanging rate (termed zero order release) giving a longer duration of activity than the same quantity of non-encapsulated oil: The above requirements will be met by our room-temperature interfacial formation of microcapsules from reagents that form polyurea or polyurethane films around dispersed oil droplets. The tough thin polyurea or polyurethane film's permeability is readily controlled by the conditions of polymerization, the composition of the reactants and the catalysts. The resultant materials are nontoxic and ultimately biodegradable.

The are many requirements needed for a micro-encapsulated essential oils formulation to be competitive, are met by the invented room-temperature interfacial formation of microcapsules from reagents that form polyurea or polyurethane films around dispersed essential oil droplets. The following requirements must be met:

1) Microcapsules must have a spherical shape, this gives the smallest surface area per unit volume that provides both efficient controlled-sustained release and maximum flow properties;
2) A nanometer to micron size is required for the capsules in order to produce an appealing homogenous readily applied formulation that does not have an unaesthetic grainy appearance or touch upon application to a given surface;
3) A microcapsule should comprise a thin external polymer membrane encapsulating a liquid core of essential oil. The polymer membrane controls the release of the oil and prevents it from being oxidized or evaporating. This configuration of liquid core encapsulated within a spherical membrane allows for an ideal constant and sustained release pattern (termed zero-order release);
4) The crosslinking density and hydrophobic/hydrophilic balance of the encapsulating membrane should be tailored to provide the required duration of control release;
5) The encapsulating membrane should be tough but not brittle to facilitate mechanical processing and to impart a smooth feel to a surface, as is required in some applications for hard surfaces and textiles;
6) Low- or room-temperature formation of the microcapsules in aqueous solutions is required to prevent alteration of oil properties at elevated temperatures and to minimize product costs;
7) Micro-encapsulation provides the surface properties such as the charge required for adsorption; and
8) To facilitate the conferring of regulatory status the encapsulating membrane and reagents used in the product should be inexpensive so as to give an economical product) non-carcinogenic and non-teratogenic and free of heavy metals.

These above-described requirements are met by our process of interfacial formation of the microcapsules using reagents that form polyurea or polyurethane membranes around dispersed oil droplets or emulsions at room temperature in aqueous solutions. The same requirements are not, however, met by the currently available techniques.

DETAILS OF THE INVENTION

The essential oils include—but not limited to—the following oils: cotton seed, soybean, cinnamon, corn, cedar, castor, clove, geranium, lemongrass, linseed, mint, sesame, thyme, rosemary, anise, basil, camphor, citronella, eucalyptus, fennel, grapefruit, lemon, mandarin, orange, pine needle, pepper, rose, tangerine, tea tree, tea seed, caraway, garlic, peppermint, onion, rosemary, citronella, lavender, geranium and almond spearmint oil. These oils may be encapsulated individually or in any combination. For example in mosquito larvicides seasame oil may be used to enhance the efficacy of pine oil, or in the case of mosquito repellents a cocktail of active ingredients such as citronella, lavender, geranium dissolved in almond oil may be encapsulated.

In addition to essential oils the liquid core may also contain adjuvants or agents which enhance the properties of the essential oils as for example sesame seed oil which contains components to enhance the properties of the essential oil to perform as larvicides or antimicrobials. The quantity of sesame oil or similar agents may vary from 2 to 80% of the liquid core composition but preferably 5 to 60%. The sesame oil acts as both a synergistic additive for the essential oil by enhancing it properties as a larvicide or antimicrobial, beyond what is possible alone. This activity of sesame oil to enhance the activity of various pesticides is well known in the state of art but has never been applied to essential oils nor to encapsulated essential oils.

The microcapsule dimensions comprising a polymeric sphere and a liquid center, range from 0.05 to 2 mm in diameter, and more preferably between 0.5 to 100 microns. To provide acceptable volatility and stability and controlled release with cost effectiveness the percentage of polymer comprising the microcapsules ranges from about 5 percent to about 90 percent by weight, preferably about 50 percent to about 85 percent by weight. For encapsulating and slowly releasing essential oils, the microcapsules have a size of at least about 0.05 micron to about 100o micron, and microcapsules in the range of about 20 to about 100 micron are particularly preferred.

Dispersion of the essential oil phase is preferably done by stirring. The stirring is preferably slowed prior to addition of polyfunctional amine to the reaction mixture. Typical initial stirring rates are from about 500 rpm to about 2000 rpm, preferably from about 1000 rpm to about 1200 rpm. Fine-tuning of diameter is achieved by controlling agitation of the reaction mixture and the nature of the components in the aqueous solutions.

In the process of making the microcapsules water immiscible essential oils with water immiscible di or poly-isocyantes dissolved within are dispersed in a aqueous phase, a water-immiscible phase consisting to form a dispersion of water-immiscible phase droplets throughout the aqueous phase; then adding, with agitation, to said dispersion a polyfunctional amine, and or polyalcohols whereby said amine and alcohol reacts with the di or polyisocyanate to form a polyurea and or polyurethane shell wall about said water-immiscible material; to aid in the suspension of the droplets in the aqueous phase emulsifiers may be used and/or a suspending agent to enhance the suspension of said microcapsules in solution.

Within the scope of this invention, polyisocyanates will be generally understood as meaning those compounds that contain two and more isocyanate groups in the molecule. Preferred isocyanates are di- and triisocyanates whose isocyanate groups may be linked to an aliphatic or aromatic moiety. Aliphatic polyisocyanates may optionally be selected from aliphatic polyisocyanates containing two isocyanate functionalities, three isocyanate functionalities, or more than three isocyanate functionalities, or mixtures of these polyisocyanates. Preferably, the aliphatic pqlyisocyanate contains 5 to 30 carbons. More preferably, the aliphatic polyisocyanate comprise one or more cycloalkyl moieties. Examples of preferred isocyanates include dicyclohexylmethane4,4'-diisocyanate; hexamethylene 1,6-diisocyanate; isophorone diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato)cyclohexane; biuret of hexamethylene diisocyanate; urea of hexamethylene diisocyanate; trimethylenediisocyanate; propylene-1,2-diisocyanate; and butylene-1,2-diisocyanate. Mixtures of polyisocyanates can be used. Examples of suitable aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate. Examples of aromatic polyisocyanates include 2,4- and 2,6-toluene diisocyanate, naphthalene diisocyanate, diphenylmethane diisocyanate and triphenylmethane-p,p',p"-trityl triisocyanate. Suitable aromatic isocyanates are toluene diisocyanate (TDI: DESMODUR Registered™ VL, Bayer), polymethylene polyphenylisocyanate (MONDUR Registered™ MR, Miles Chemical Company); PAPI Registered™ 135 (Dow Company), 2,4,4'-diphenyl ether triisocyanate, 3,3'-dimethyl-4,4'-diphenyl diisocyanate, 3,3'-dimethoxy-4,4'diphenyl diisocyanate, 1,5-naphthalene diisocyanate and 4,4',4"-triphenylmethane triisocyanate. A further suitable diisocyanate is isophorone diisocyanate. Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked urethane groups to the polyhydric alcohol to form high molecular polyisocyanates. Another suitable product of this kind (BESMODUR Registered™ L) can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenylisocyanate. The di- and triisocyanates specified above can be employed individually or as mixtures of two or more such isocyanates.

In one preferred embodiment polyisocyanates are polymethylene polyphenylisocyanates. These compounds are available under the trademark Mondur-MRS. The mole equivalent ratio of total primary amine or hydroxyl functionality to isocyanate functionality in the system is preferably about 0.8:1 to 1:1.2, and more preferably about 1:1.1.

Said polyfunctional amine can be any of the polyamines taught for this purpose in the prior art and and amines used in this invention are for the formation of a polyurea skin. The diamines or polyamines (e.g. ethylene diamine, phenylene diamine, toluene diamine, hexamethylene diamine, Said polyfunctional amine can be any of the polyamines taught for this purpose in the prior art and di-, tri-, tetra- or penta-amines are especially preferred. For example Ethylene diamine, Diethylene triamine Propylene diamine Tetra ethylene penta amine, pentamethylene hexamine and the like) are present in the water phase and are present in the organic/oil phase. Suitable polyamines within the scope of this invention will be understood as meaning in general those compounds that contain two or more primary amino groups in the molecule, which amino groups may be linked to aliphatic and aromatic moieties. Examples of suitable aliphatic polyamines are alpha, omega-diamines, including, without limitation, ethylenediamine, propylene-1,3-diamine, tetramethylenepentamine, pentamethylenehexamine and 1,6-hexamethylenediamine. A preferred diamine is 1,6-hexamethylenediamine.

Further suitable aliphatic polyamines are polyethyleneamines, including, without limitation, diethylenetriamine, triethylenetriamine, tetraethylenepentamine, pentaethylenehexamine.

Examples of suitable aromatic polyamines are 1,3-phenylenediamine, 2,4-toluylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetraaminoanthraquinone. Those polyamines which are insoluble or insufficiently soluble in water may be used as hydrochloride salts.

Also useful are compounds whose structure is similar to the above, but which have one or more oxygen atoms present in ether linkages between carbon atoms. It is preferred that hydrogen, is present on the amines especially at the terminal amino groups. Aromatic diamines, for example toluene diamine, can be used. Mixtures of polyfunctional compounds can be used.

Further suitable polyamines are those that contain sulfo or carboxyl groups in addition to the amino groups. Examples of such polyamines are 1,4-phenylene diaminesulfonic acid, 4,4'-diaminodiphenyl-2-sulfonic acid, or diaminocarboxylic acids such as ornithene and lysine.

Such amino compounds which also contain anionic or cationic or amphoteric or hydrophilic groups which render the surface of the encapsulated essential oil microcapsules anionic, cationic or amphoteric or hydrophilic but non-charged.

The di or polyhydroxy compounds which may react with the isocyanate groups to form urethane groups may be chosen from polyhydric alcohols, such as ethylene glycol, diethylene glycol, propylene glycol, 1,4-butane diol, 1,4 hexane diol, dipropylene glycol, cyclohexyl 1,4 dimethanol, 1,8 octane diol and polyols such as poly(ethylene glycols), poly(propylene glycols), poly(tetramethylene glycols) with average molecular weights in the range of 200-2000. The preferred crosslinkers are compounds containing more than two hydroxyl functionalities, for example, trimethylolpropane, glycerol, hexane, triols and pentaerythrytol. The amount of crosslinker used based on diol is in the range of 5-40 wt. %, preferably 10 to 20 wt. %. Aromatic hydroxyl compounds may be chosen from 1,3-phenylenedihydroxy, 2,4-toluylenedihydroxy, 4,4'-dihydroxydiphenylmethane, 1,5-dihydroxyoaphthalene, 1,3,5-trihydroxybenzene, 2,4,6-trihydroxytoluene, 1,3,6-trihydroxynaphthalene, 2,4,4'-trihydroxydiphenyl ether. Reagents with hydroxyl groups which also contain carboxylic acid, sulfonic phosphonic, and quaternary ammoniums may also be used to render the surface of the encapsulated essential oil microcapsules anionic, cationic or amphoteric or non-charged hydrophilic.

Catalysts may be added to the essential oil or the aqueous solution to enhance the reactivity of the isocyanate with the amines or hydroxyl groups. Catalysts suitable for use in the invention are amino or organometallic compounds such as N,N-dimethylaminoethanol, N—N-dimethylcyclohexylamine, bis-(2-dimethylaminoethyl)ether, N,N dimethylcetylamine, diaminobicyclooctane, stannous octoate and dibutyltin dilaurate having concentration 0.1-0.3 wt. % based on diol.

And metal salts, tertiary amines and the like. For example triethylamine or diethylmethyl amine and metal salts of Cu, Pb, Zn, Co, Ni, Mn.

To form dispersions emulsifiers may be used such as sodium, potassium, magnesium, calcium or ammonium salts of lignin sulfonate.

Suspending agent to enhance the suspension of said microcapsules in solution are preferably said non-basic emulsifier is selected from the group consisting of low and high density polyvinylalcohol, or Tween 20, 40 or 80 and said suspending agent is selected from the group consisting of carboxymethyl cellulose, sodium salt, Xanthan gum, Karya gum and Locust bean gum.

Preferably said non-basic emulsifier is selected from the group consisting of low and high density polyvinylalcohol, or Tween 20, 40 or 80 and said suspending agent is selected from the group consisting of carboxymethyl cellulose, sodium salt, Xantan gum, Karya gum and Locust bean gum.

A surfactant is required for the aqueous dispersion. Preferably it is a nonionic surfactant. As examples of suitable surfactants there are mentioned polyvinylpyrrolidone (PVP), polyvinyl alcohol (PVA) and poly(ethoxy)nonylphenol. PVP is available at various molecular weights in the range of from about 20,000 to about 90,000 and all these can be used, but PVP of about 40,000 molecular weight is preferred. Poly (ethoxy)nonylphenols are available under the trade-mark Igepal, with various molecular weights depending on the length of the ethoxy chain. Poly(ethoxy)nonylphenols can be used but Igepal 630, indicating a molecular weight of about 630, is the preferred poly(ethoxy)nonylphenol. Other examples of surfactants include polyether block copolymers, such as Pluronic™ and Tetronic™, polyoxyethylene adducts of fatty alcohols, such as Brij™ surfactants, and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as Arlacel C® surfactants.

Surfactants vary in their surfactant properties, and the surfactant properties affect the size of the microcapsules formed. Other things being equal, use of PVP of 40,000 molecular weight will give larger microcapsules than Igepal 630. The surfactant used, and also the degree and extent of agitation, affect the size of the microcapsules obtained. In general, they may be from about 1 to about 100 micron in size, depending upon the conditions used.

Although less preferred, ionic surfactants can be used. Mention is made of partially neutralized salts of polyacrylic acids such as sodium or potassium polyacrylate or sodium or potassium polymethacrylate.

As the water-immiscible solvent there is used a non-polar solvent that is inert to the encapsulation reaction, but in which the polyisocyanate and the material to be encapsulated can be dissolved or suspended. As suitable solvents there are mentioned hydrocarbon solvents, for example kerosene and alkyl benzenes such as toluene, xylene, and the like. It is desirable to use only a small amount of the solvent; amounts up to about 5%, based on the amount of water, usually suffice and in most cases it is preferred to use the solvent in an amount of about 3% or less.

The reaction proceeds readily at room temperature, but it may be advantageous to operate below room temperature, down to about 0° C., preferably at about 15° C. There may be cases that the reaction temperature is carried out at elevated temperatures of up to 70° C. but the preferred temperature range is between 0° C. to 30° C. and most preferred below 20° C.

The microcapsules can be suspended in water to give a suspension suitable for aerial spraying. The suspension may contain a suspending agent, for instance a gum suspending agent such as guar gum, rhamsan gum or xanthan gum.

Incorporation of a light stabilizer, if needed, is within the scope of the invention, however. Suitable light stabilizers include the tertiary phenylene diamine compounds disclosed in Canadian Patent No. 1,179,682, the disclosure of which is incorporated by reference. The light stabilizer can be incorporated by dissolving it, with the essential oil and polyisocyanate, in the water-immiscible solvent. Alternatively, a light stabilizer can be incorporated in the polyurea shell as taught in Canadian Patent No. 1,044,134, the disclosure of which is also incorporated by reference.

The capsules are prepared from various di- and polyisocyanates in a dispersed organic phase. Some of the isocyanate present reacts to yield an amine which reacts further with remaining isocyanate at the interface with water and subsequently polymerizes to form a polyurea shell. The aqueous phase also containing surfactant, for example an ethoxylated nonylphenol or a polyethylene glycol ether of a linear alcohol. In addition, the aqueous phase contains protective colloids, typically polyacrylates, methylcellulose and PVA. Particle sizes as low as 1 micron are exemplified.

In one preferred embodiment of this invention the encapsulation is carried out by dissolving a polyisocyanate (in one preferred case based on bisphenol A) into the essential oil, emulsifying this mixture in water containing a di or poly alcohol (ex. polyethylene glycol [PEG]). A preliminary reaction occurs which forms a membrane and results in primarily a polyurethane encapsulating coating with minimal urea groups which may form by hydrolysis of the isocyanate with the water and the resulting amines reacting with remaining isocyanate groups. The final product contains only the microcapsules dispersed in water with no toxic chemical left. The solution is not further purified and other materials are added constitute the final formulation.

One preferred material for incorporating into the encapsulating membrane during the interfacial polymerization and or as an adjuvant or additive to the aqueous solution is polyvinyl alcohol. Polyvinyl alcohols have been claimed in encapsulation of synthetic pesticides. For example In a recent patent assigned to Dow U.S. Pat. No. 5,925,464 Jul. 20, 1999 Mulqueen; Patrick Joseph; Smith; Geoff); Lubetkin; Steven D small micro-encapsulated pesticides (ex Chlorpyrifos) formulations could be made by encapsulated including PVA together with a polyamine (ex Diethylene triamine) in the aqueous phase for an interfacial polycondensation reaction with polyisocyanates (ex Voranate M220) for producing microcapsules. Microcapsules can be obtained which show improved storage stability, especially to the leaching of the active material from the resulting microcapsules, particularly when the microcapsules are small in size, (for example less than 5 micrometer).

As stated in said patent and incorporated in the present invention "An advantage of the encapsulation method in which the PVA is present during the encapsulation reaction, is that by altering the time before the addition of the polyamine, the amount of polyurethane and polyurea in the capsule wall can be controlled with some accuracy. Since these two polymers have very different diffusivities for the encapsulated material, this ratio of polyurethane/polyurea provides a further, independent method for controlling the release rate of the active, in addition to the control provided by varying capsule wall thickness and capsule size. An additional advantage of using PVA during the encapsulation reaction is that PVA pendants form on the surface of the microcapsule which act as a steric barrier doewards aggregation during production or storage, and enhance both the efficency of spray drying and the rapid dispersion of the dry product into water when needed".

U.S. Pat. No. 4,417,916 discloses encapsulation of water-immiscible materials such as herbicides in a polyurea shell. A polyisocyanate and a polyamine are used to form the polyurea, and the invention appears to reside in the use of a lignin sulfonate compound as emulsifier in the polyurea-forming reaction. The concentration range of water-immiscible material encapsulated in the examples listed is 320 to 520 g/L of composition.

U.S. Pat. No. 4,563,212 is similar in teaching to U.S. Pat. No. 4,417,916, but uses emulsifiers other than lignin sulfonates, particularly sulfonated naphthalene formaldehyde condensates and sulfonated polystyrenes.

European Patent No. 611 253 describes reaction of polyisocyanates and polyamines to encapsulate materials such as pesticides in polyurea, using nonionic surfactants that are block copolymers containing hydrophillic blocks together with hydrophobic blocks.

In one described embodiment, a polyamine in the form of a salt is added to a dispersion of isocyanate, to allow polymerization to be initiated by addition of a base. It is said that this may improve the stabilization of behaviour modifying compounds that are aldehydes, but this is not exemplified.

In one preferred embodiment the encapsulated material is a partially water-miscible material and the amount of the partially water miscible material encapsulated is at least 5%, preferably at least 90%, based on the total weight of microcapsules.

In another aspect the invention provides microcapsules composed of a partially water-miscible organic material of molecular weight greater than about 100 and less than about 400 and containing at least one heteroatom, encapsulated within a polyurea or polyurethane shell, the amount of the said material encapsulated being at least 5%, preferably at least 9%, based on the total weight of the microcapsules.

The encapsulating walls of the microcapsules are made of a polymer which may have different degrees of porosity and pore size. The pore size and porosity may be varied by well known methods and the said pore size may be varied from micron to submicron pores to nano scale pores, and in one preferred application may be a relatively dense barrier where the transport across the barrier is by a "solution-diffusion mechanism. The polymer walls of this invention may be chosen from, such polymers as polyurea, polyamide, polysulfonamide, polyester, polycarbonate, or polyurethane and comprise from about 5 percent to about 35 percent by weight of each microcapsule. Preferably, the walls of the microcapsule comprise from about 10 percent to about 25 percent by weight of the microcapsule.

The emulsifier is preferably selected from the group of the salts of ligninsulfonic acid, such as, for example, the sodium, potassium, magnesium, and calcium salts thereof. Particularly effective is the sodium salt of ligninsulfonic acid, which is referred to herein as a lignosulfonate emulsifier or surfactant.

In another embodiment of the present invention, the microcapsule preparation comprises an aqueous phase comprised of a solution containing a suitable emulsifier/cross-linking resin, an optional stabilizer in the form of an anti-foam agent, and an optional anti-microbial agent. The emulsifier/cross-linking resin is preferably derived from the copolymerization product of styrene and maleic anhydride, or derived from the copolymerization product of styrene, maleic anhydride and an alcohol. The copolymerization of styrene and maleic anhydride provides a non-esterified or anhydride copolymer. When the copolymerization of styrene and maleic anhydride is conducted with an alcohol, the maleic anhydride rings open to form a copolymer that is a half-acid and half-ester of the corresponding alcohol that is in the copolymerization reaction. Such alcohols include, without limitation, straight or branched chain lower $C_1$-$C_6$ alkyl alcohols. The anhydride copolymers and the half acid/half ester copolymers are further reacted with hydroxides such as ammonium hydroxide, sodium hydroxide, potassium hydroxide, magnesium hydroxide, calcium hydroxide, and the like, to provide the aforementioned resins in the form of water-soluble salts. Reaction of the aforementioned hydroxides with the anhydride copolymer causes the maleic anhydride rings to open to provide a di-salt, for example, a di-sodium, salt or a di-potassium salt. When the anhydride copolymer is reacted with, for example, ammonium hydroxide, the maleic anhydride rings open to provide an amide/ammonium salt. In the context of the present invention, the emulsifier/cross-linking resin is preferably selected from the ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half-acid/half-ester copolymerization product of styrene and maleic anhydride. Particularly preferred resins are the ammonium hydroxide and sodium hydroxide salts of an anhydrous copolymerization product of styrene and maleic anhydride, most preferred is the ammonium hydroxide salt.

Adjuvants that can be added to the solution of microcapsules to improve shelf life, and/or sprayability, and or performance characteristics such as adsorption to a substrate, can be chosen from both natural and synthetic polymers such as polyvinyl alcohol, polyvinylpyrrolidone, polyethylene oxides, ethylene/maleic anhydride copolymer, methyl vinyl ether-maleic anhydride copolymer, water-soluble cellulose, water-soluble polyamides or polyesters, copolymers or homopolymers of acrylic acids, water-soluble starches and modified starches, natural gums such as alginates, dextrins and proteins such as gelatins and caseins.

As will be realised while the present invention is directed primarily to a process for the preparation of essential oil microcapsules it is also directed to essential oil microcapsules when prepared by any of the processes according to the present invention described herein and is also specifically directed to essential oil microcapsules whenever prepared by any of the processes of the present invention and whenever used in any of the following applications: Disinfectant and sanitizing compositions for hard surfaces such as counter tops, tiles, porcelain products (sinks and toilets), floors, windows, cutlery, glassware, dishes and dental and surgical instruments; Fragrance and skin-benefit liquids for application to textile structures to improve physiological conditions of the skin; Antimicrobial wipes that provide improved immediate germ reduction; Leave-on antimicrobialcompositions for gram negative and gram positive bacteria; Disinfectant and sanitizing compositions; Blooming agents_in germicidal hard surface cleaning compositions; Liquid detergent compositions; Antimicrobial compositions with antiseptic, antiviral and larvicidal activity as treatments for cold sores, head lice, vaginal thrush, verruca, warts, and athlete's foot and as antimicrobial mouth washes and surface cleaners; Lice treatment; Natural pesticides; Flavoring agents; Fragrances; Treatment of infections in man and animals; Lice repellant composition; Analgesic and antiphlogistic compositions; Fragrance or insect-repellant agent; Active agents in pharmaceuticals and cosmetics; Benefit agent in extruded soap and/or detergent bars; Food or tobacco additive; Active agents in Pharmaceuticals and Cosmetics; Hair care products; and Dentifrice containing encapsulated flavoring. Mosquito, ants and insect repellents; Mosquito larvicides; Anti viral agents; Anti fungal agents; Gels against gum diseases; Tampons for feminine use safe from toxic syndromes; and Diapers.

While the invention will now be described in connection with certain preferred embodiments in the following examples so that aspects thereof may be more fully understood and appreciated, it is not intended to limit the invention to these particular embodiments. On the contrary, it is intended to cover all alternatives; modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Formation of essential oil microcapsules is carried out by interfacial polymerization as follows using the composition 1 in Table 1 by mixing 13.5 gr isocyanates into 88 gr Eucalyptus oil and adding this to 347 grams water containing the amines EDA and DETA using a high sheer mixer. The mixing was continued fro two hours at room temperature and then the dispersant a Xanthane gum [Rodopol] (1.35 grams) to achieve a stable emulsion and the pH adjusted to 7.0 as needed. This formulation had 100% mortality against mosquito larvae culex pipiens after day at 500 ppm.

Example 2

Example 1 is repeated using TDI [see formulation 2 in Table 1] instead of Voronate M-580 the resulting capsules had no mortality even after 1 day at 500 ppm showing how the choice of materials which go into making the encapsulated formulation is important.

Example 3

Example 2 is repeated using Pine oil [see formulation 3 Table 1]. The resultant encapsulation gave a 78% yield with an average of a 100 micron sized capsules.

Example 4

Example 1 is repeated using Pine oil [see formulation 3 Table 1]. The resultant encapsulation gave a 85% yield with an average of a 50 micron sized capsules.

Example 5

Example 2 is repeated using Pine oil with 3.4 gr TDI and 0.75 gr EDA and 0.68 gr DETA [see formulation 5 Table 1]. The resulting capsules had a 97% mortality after one day at 500 ppm against mosquito larvae culex pipiens.

Example 6

Example 5 is repeated using Pine oil with 44 gr Voronate M-580 instead of TDI and 0.75 gr EDA and 0.68 gr DETA [see formulation 6 Table 1]. The resulting capsules had a 97% mortality after one day at 500 ppm against mosquito larvae culex pipiens.

Example 7

Example 4 is repeated using Pine oil and Voronate M 580 and TEPA and HMDA instead of EDA and DETA [see formulation 7 Table 1]. The resulting capsules had only 10% mortality after one day at 500 ppm against mosquito larvae culex pipiens.

Example 8

Example 7 is repeated using Pine oil and replacing the Voronate M 580 with TDI [see formulation 8 Table 1]. The resulting capsules had only 53% mortality after one day at 500 ppm against mosquito larvae culex pipiens.

Example 9

Example 4 is repeated using Pine oil and Voronate M 580 and PEG 4000 instead of an amine [see formulation 9 Table 1]. The resulting capsules had only 7% mortality after one day at 500 ppm against mosquito larvae culex pipiens.

Example 10

Example 9 is repeated using TDI instead of Voronate M 580 [see formulation 10. Table 1]. The resulting capsules had 100% mortality after one day at 500 ppm against mosquito larvae culex pipiens tested in 100 liter barrels.

Example 11A

Example 10 is repeated using different concentrations of TDI and PEG 4000 [see formulation 11 Table 1]. The resulting capsules were tested in barrels of 100 liters and had 87% and 100% mortality after one day at 800 and 1000 ppm respectively against mosquito larvae culex pipiens. After 14 and 20 days the % mortality for the 1000 ppm concentration was 87% and 80% respectively.

Example 11B

When example 11A is repeated with 500 ppm of a partially quaternized tetraethylene penta-amine the resulting encapsulated formulation had a 95% and 90% mortality rate against mosquito larvae culex pipiens after 14 and 20 days. Indicating an improved efficacy for microcapsules with a cationic surface.

Example 12A

When the encapsulated pine oil made in example 11 was tested in a 70 liter pond. At a 800 ppm concentration for 1, 7, 13 and 21 days the average % mortality against mosquito larvae culex pipiens for three different ponds was averaged 98%, 53%, 66% and 39% respectively. Pine oil without encapsulation at the same 800 ppm concentration had only 8% mortality after the first day and 0% thereafter. At 400 ppm the % mortality was 93% and 43% after 1 and 7 days respectively.

Example 12B

When the above encapsulation of pine oil as in example 12A also contained sesame oil [10% by weight of the total liquid core of pine oil and sesame oil] a 800 ppm concentration of the encapsulated mixture for 1 and 7 days had on the average of three separate ponds 93% and 89% mortality against mosquito larvae culex pipiens. The non-encapsulated Pine/Sesame oil had a mortality rate of 23% and 7% after 1 and 7 days respectively. This indicated the significant better effects of the mixture of pine oil and sesame oil rather than the sesame oil alone.

Example 13

Example 11 is repeated using PEG 2000 instead of PEG 4000 and a higher concentration of TDI [see formulation 12 Table 1] and was tested in a 70 liter pond at 400 ppm and gave a 70 to 73% mortality against mosquito larvae culex pipiens. Pine oil without encapsulation at the same 400 ppm concentration had only 7% mortality.

Example 14

The above example 1 was repeated with clove oil with an encapsulation efficiency was 83%.

Example 15

Micro-encapsulated essential oil formulation prepared in Example 11 with TDI and PEG 4000 [Formulation 13 Table 1] and were were placed in shallow 70 liter water bath at a concentration of 800 ppm and showed an 90% kill effect on mosquito larvicides *A. aegypti* and *Culex pipiens* while the control of non-encapsulated oil was only 10% after 1 day. These results can be compared to a number of tests carried out with other larvicides: for example, saponin extracts from *Quillaja saponaria,* 800 ppm gave 100% larval mortality against *A. aegypti* and *Culex pipiens* after 1 to 5 days. Tests with cyromazine, an insect growth regulator produced by Novartis, was tested for larvicidal activity, either as such or in encapsulated form An effective concentration of 0.5 g/m² of cyromazine gave 60% mortality after 3 days, and the best sustained-release formulation gave. 100% mortality after 8 days.

Example 16

Microcapsules of eucalyptus oil were made according to example 2 and applied under conditions at which fabric softeners are used have a substantial disinfectant efficacy against the two microorganisms tested (*Staphylococcus aureus* and *Escherichia coli*) at low temperatures. At a concentration of 0.8%, more than 99% of the bacteria were killed. There was a strong concentration effect on efficacy: in increasing the concentration of active ingredient from 0.2% to 0.8%, the population of microorganisms killed increased by a factor of 1 million. In contrast, oxycarbonates, which are currently used as a substitute for chlorine-based disinfectants in Europe, have very limited efficacy against microorganisms at room temperature.

Example 17

Microcapsules of eucalyptus oil were made according to example 1 and applied to a brick wall at a concentration of 1.0 grams per meter square of wall area [based on the essential oil weight] were shown to have substantial disinfectant efficacy against the two microorganisms tested (*Staphylococcus aureus* and *Escherichia coli*) at low temperatures—killing more than 95% of the bacteria.

Example 18

Microcapsules of eucalyptus oil were made according to example 2 and applied to a marble floor at a concentratio of 8 grams per meter square of floor area [based on the essential oil weight] were shown to have substantial disinfectant efficacy against the two microorganisms tested (*Staphylococcus aureus* and *Escherichia coli*) at low temperatures—killing more than 90% of the bacteria.

TABLE 1

Material Compositions for Forming Encapsulated Essential Oils

| | | Isocyanate | | | Amines grams | | | | | |
|---|---|---|---|---|---|---|---|---|---|---|
| | | Voronate | | | | | | | | |
| No. | Essential oil | M-580 (DOW)[1] gr | TDI[2] gr | Water grams | PEG 2000 | PEG 4000 | EDA | DETA | TEPA | HMDA | Dispersant |
| 1 | Eucalyptus 88 g | | 13.5 | 347 | | | 3 | 2.7 | | | Rodopol 1.35 gr |
| 2 | Eucalyptus 88 g | 17.5 | | 307 | | | 3 | 2.7 | | | Rodopol 1.35 gr |
| 3 | Pine 88 g | | 13.5 | 347 | | | 3 | 2.7 | | | Rodopol 1.35 gr |
| 4 | Pine 88 g | 17.5 | | 307 | | | 3 | 2.7 | | | Rodopol 1.35 gr |
| 5 | Pine 88 g | | 3.4 | 362 | | | 0.75 | 0.68 | | | Rodopol 1.5 gr |
| 6 | Pine 88 g | 4.4 | | 361 | | | 0.75 | 0.68 | | | Rodopol 1.5 gr |
| 7 | Pine 90 g | 17 | | 370 | | | | | 3.2 | 2 | JR-30 1.5 g |
| 8 | Pine 90 g | | 13.5 | 374 | | | | | 3.2 | 2 | JR-30 1.5 g |
| 9 | Pine 70 g | 13.2 | | 262 | | | | | | | JR-30 1.2 g |
| 10 | Pine 70 g | | 10.2 | 265 | | 16.3 | | | | | JR-30 1.2 g |
| 11 | Pine 420 g | | 61.2 | 1591 | | 97.8 | | | | | JR-30 1.5 g |
| 12 | Pine 420 g | | 88.7 | 1590 | 71 | | | | | | JR-30 8.2 gr |
| 13 | Pine 420 g | | 61.2 | 1591 | | 97.8 | | | | | JR-400 8.2 gr |

[1]Copolymer 4,4' diphenylmethane diisocyanate
[2]Toluene diisocyanate (Fluka)
PEG = polyethylene glycol
EDA = ethylene diamine
DETA = diethylene triamine
TEPA = tetraethylene pentaamine
HMDA = hexamethylene diamine
Rodopol = Xanthane gum
JR = cation hydroxy ethyl cellulose polymer from Amerchol of Edison NJ USA

Example 19

In this example the application of encapsulated essential oils as mosquito repellents is demonstrated.

A cocktail of the three essential oils citronella, lavender, geranium in a ratio of 1:1:1 as a cocktail of active ingredients are dissolved in almond oil to form a 24% solution of active ingredients supplied by Tamar LTD of Israel with the trade name Di-Tush is encapsulated according to procedure 1 above using the following combination. Thus 153 grams of Di-Tush with an active essential oil concentration of 24% is mixed with 19.8 grams of TDI and this is dispersed in an aqueous solution of 270 grams water, with 2.7 gr PVA. About 5 minutes after the microcapsules are formed 32.3 grams of PEG 4000 dissolved in 75 grams of water and the dispersion continued, finally at the end of the preparation Nefocide 2.4 grams, Rodopol 0.7 grams and Sodium di-hydrogen phosphate are added. This formulation is called N141. The results on two human volunteers is given in Table 2.

The Relative Efficacy of repellant #141 against *Aedes aegypti* for an 8 hour exposure period (8:30 to 16:30)

| Repellent # | Reduction of mosquito bites (%) during 10 min in mosquito cages each hour for 8-hr exposure | | | | | | | |
|---|---|---|---|---|---|---|---|---|
| 141 | 1 | 2 | 3 | 4 | 5 | 6 | 7 | 8 |
| Human volunteer N1 | | 94.3 | 91.7 | 84.1 | 77.9 | 78.4 | 78.3 | 77 |
| Human volunteer N2 | 100 | 100 | 96.3 | 96.7 | 93.5 | 92.3 | 90.1 | |
| Average | | 97.1 | 95.8 | 90.2 | 87.3 | 85.9 | 85.3 | 83.9 |

The percentage reduction in mosquito bites on the forearm of human volunteer during 10 minutes in mosquito cages each hour for 8 h exposure of test was calculated according to the formula: Percentage reduction = 100 × (C − T)/C
Where C is the number of mosquito bites on the forearm of the human volunteer during 10 minutes in untreated mosquito cage each hour and T is the number of mosquito bites on the forearm on the human volunteer during 10 minutes in treated I mosquito cage each hour.

Example 20

The above example 19 is repeated to give additional formulation #141 and another formulation using a Di-Tush formulation with a 48% active concentration to give formulation #143 is made in the same way. Both formulations are tested on mice together with a commercially available synthetic mosquito repellent MO438E (29% a.i.) The results are given in Table 3. The results show for both formulations a good mosquito repellancy.

TABLE 3

The Relative Efficacy of repellant #141 against *Aedes aegypti* for an 8 hour exposure period (8:30 to 16:30)

| Repellent | Reduction of mosquito bites (%) the tree treated mice during 8-hr exposure | | | | | | | |
|---|---|---|---|---|---|---|---|---|
| | 1 | 2 | 3 | 4 | 5 | 6 | 7 | 8 |
| MO438E (20% a.i.) | 100 | 98.8 | 100 | 100 | 100 | 100 | 100 | 98.9 |
| #141 (6% a.i.) | 100 | 100 | 100 | 100 | 99.4 | 99.1 | 100 | 98.9 |
| #143 (6% a.i.) | 100 | 100 | 100 | 100 | 100 | 100 | 100 | 98.9 |

The percentage reduction in landing mosquitos bites on the three mice during every hour of test was calculated according to the formula: Percentage reduction = 100 × (C − T)/C
Where C is the number of landed mosquitos on the three untreated control mice during each hour in the untreated control mosquito cage and T is the number of landed mosquitos on the three treated mice volunteer during each hour in treated mosquito cages.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process to produce essential oils microcapsules suitable for use as disinfectants, pesticides, insect repellants, antiviral and/or antifungal agents, the process comprising the steps of:
   (a) dissolving a di- or polyisocyanate into a volatile essential oil to form a non-aqueous mixture;
   (b) emulsifying the non-aqueous mixture in an aqueous solution comprising a di- or polyamine, and/or a di- or polyhydroxy compound and at least one non-basic emulsifier selected from the group consisting of low density polyvinyl alcohol, high density polyvinyl alcohol, Tween 20, Tween 40 and Tween 80 to effect encapsulation of the essential oil through interfacial polymerization, the interfacial polymerization carried out at a temperature of between 0° C.-30° C.,
   wherein steps (a) and (b) form microcapsules comprising a polyurea and/or polyurethane shell encapsulating the essential oil droplets,
   wherein the microcapsules comprise 60 to 95% essential oil, and wherein the microcapsules after formation, are reacted with reactive amine or hydroxyl containing reagents which also contain anionic, cationic, amphoteric or hydrophilic groups which render the surface of the microcapsules anionic, cationic, amphoteric or non-charged hydrophilic.

2. The process according to claim 1, wherein the aqueous solution further comprises a di- or polyalcohol.

3. The process according to claim 2, wherein the di- or polyalcohol is selected from the group consisting of polyhydric alcohols, polyols, triols and pentaerythrytol, 1,3-dihydroxyphenylene, 2,4-toluylenedihyroxy 2,4-dihyroxytoluene, 4,4'-dihydroxydiphenylmethane, 1,5-dihydroxynoaphthalene, 1,3,5-trihydroxybenzene, 2,4,6-trihydroxytoluene, 1,3,6-trihydroxynaphthalene, 2,4,4'-trihydroxydiphenyl ether and polyvinyl alcohols.

4. The process according to claim 1, wherein the essential oil is encapsulated together with a further component selected from the group consisting of an adjuvant and an agent which enhances the properties of the essential oil.

5. The process according to claim 1, wherein the essential oil is selected from the group consisting of cotton seed, soybean, cinnamon, corn, cedar, castor, clove, geranium, lemongrass, linseed, sesame, thyme, rosemary, anise, basil, camphor, citronella, eucalyptus, fennel, grapefruit, lemon, mandarin, orange, pine needle, pepper, rose, tangerine, tea tree, tea seed, caraway, garlic, peppermint, onion, lavender, almond, spearmint and mixtures thereof.

6. The process according to claim 1, wherein the aqueous solution further comprises a di- or polyalcohol which in a slower reaction forms an exterior crosslinked coating, and wherein any remaining isocyanate is further consumed by water to form amine which reacts with any remaining isocyanate.

7. The process according to claim 1, wherein the di- or polyisocyanate is selected from the group consisting of dicyclohexylmethane 4,4'-diisocyanate, hexamethylene 1,6-diisocyanate, isophoronediisocyanate, trimethyl-hexamethylenediisocyanate, trimer of hexamethylene 1,6-diisocyanate, trimer of isophoronediisocyanate, 1,4-cyclohexane diisocyanate, 1,4-(dimethylisocyanato)cyclohexane, biuret of hexamethylenediisocyanate, urea of hexamethylenediisocyanate, trimethylenediisocyanate, propylene-1,2-diisocyanate, a butylene-1,2-diisocyanate mixture of aliphatic diisocyanates and aliphatic triisocyanates, an aromatic polyisocyanate, an aromatic isocyanate.

8. The process according to claim 7, wherein the butylene-1,2-diisocyanate mixture of aliphatic diisocyanates and aliphatic triisocyanates is selected from the group consisting of tetramethylenediisocyanate, pentamethylenediisocyanate, hexamethylenediisocyanate and 4-(isocyanatomethyl)-1,8-octyl diisocyanate.

9. The process according to claim 7, wherein the aromatic isocyanate is selected from the group consisting of 2,4- and 2,6-toluene diisocyanate, naphthalene diisocyanate, diphenylmethanediisocyanate and triphenylmethane-p,p',p"-trityltriisocyanate.

10. The process according to claim 7, wherein the aromatic isocyanate is selected from the group consisting of toluene disiocynate, polymethylenepolyphenylisocyanate, 2,4,4'-diphenyl ether triisocyanate, 3,3'-dimethyl-4,4'diphenyl diisocyanate, 3,3'-dimethoxy-4,4'diphenyl diisocyanate.

11. The process according to claim 1, wherein the diamine or polyamine is selected from the group consisting of ethylenediamine, diethylenetriamine, propylenediaminetetraethylenepentaamine, pentamethylene hexamine, alpha, omega-diamines, propylene-1,3-diamine, tetramethylenediamine, pentamethylenediamine and 1,6-hexamethylenediamine polyethyleneamines, triethylenetriamine, pentaethylenehexamine, 1,3-phenylenediamine, 2,4-toluylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetraaminoanthraquinone.

12. The process according to claim 1, further comprising adding, to the aqueous solution into which the essential oil mixture is dispersed, a component to prevent or reduce microcapsule particle aggregation, the component being selected from the group consisting of an emulsifier, a suspending agent and a steric barrier polymer.

13. The process according to claim 12, wherein the steric barrier is selected from the group consisting of sodium, potassium, magnesium, calcium or ammonium salts of lignin sulfonate, low density polyvinylalcohol, high density polyvinylalcohol, Tween 20, Tween 40 and Tween 80.

14. The process according to claim 12, wherein the suspending agent is selected from the group consisting of carboxymethyl cellulose, sodium salt, Xantan gum, Karya gum, Locust bean gum, polyvinylpyrrolidone (PVP), water soluble polyvinyl alcohol (PVA), poly(ethoxy)nonylphenol, polyether block polymers, polyoxyethylene adducts of fatty alcohols and esters of fatty acids.

15. The process according to claim 1, wherein the microcapsules possess sustained anti-microbial activity when used in hard surface cleaners, laundry detergents and softeners and/or as a food additive.

16. The process according to claim 1, wherein the microcapsules, after formation, are post modified by absorbing onto their surfaces monomers or polymers which increase the hydrophilicity or hydrophobicity of the microcapsule and/or render the surfaces of the microcapsules anionic, cationic, amphoteric or non-charged hydrophilic.

17. The process according to claim 1, wherein the microcapsules are suitable for use as disinfectants, pesticides, insect repellants, antiviral and/or antifungal agents.

18. The process according to claim 1, wherein the shell has a permeability facilitating sustained release of the essential oil.

* * * * *